United States Patent
Kida et al.

(10) Patent No.: US 11,266,671 B2
(45) Date of Patent: *Mar. 8, 2022

(54) COMPOSITIONS OF O-GLYCOSYL FLAVONOIDS

(71) Applicant: Alps Pharmaceutical Ind. Co., Ltd., Gifu (JP)

(72) Inventors: Hiroaki Kida, Gifu (JP); Naoto Yamaguchi, Gifu (JP); Mitsunori Ono, Nagano (JP)

(73) Assignee: ALPS Pharmaceutical Ind. Co., Ltd., Gifu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/497,746

(22) PCT Filed: Apr. 23, 2019

(86) PCT No.: PCT/JP2019/017262
§ 371 (c)(1),
(2) Date: Sep. 25, 2019

(87) PCT Pub. No.: WO2019/208574
PCT Pub. Date: Oct. 31, 2019

(65) Prior Publication Data
US 2021/0379093 A1    Dec. 9, 2021

Related U.S. Application Data

(60) Provisional application No. 62/720,651, filed on Aug. 21, 2018, provisional application No. 62/661,255, filed on Apr. 23, 2018.

(51) Int. Cl.

| | | |
|---|---|---|
| A61K 31/7048 | (2006.01) | |
| A61K 9/08 | (2006.01) | |
| A61K 31/198 | (2006.01) | |
| A61K 31/375 | (2006.01) | |
| A61K 31/455 | (2006.01) | |
| A61K 31/51 | (2006.01) | |
| A61K 31/519 | (2006.01) | |

(52) U.S. Cl.
CPC ............ *A61K 31/7048* (2013.01); *A61K 9/08* (2013.01); *A61K 31/198* (2013.01); *A61K 31/375* (2013.01); *A61K 31/455* (2013.01); *A61K 31/51* (2013.01); *A61K 31/519* (2013.01)

(58) Field of Classification Search
None
See application file for complete search history.

(56) References Cited

U.S. PATENT DOCUMENTS

| | | |
|---|---|---|
| 2,451,772 A | 10/1948 | Plungian et al. |
| 2,646,428 A | 7/1953 | Chabrier |
| 2,975,168 A | 3/1961 | Favre et al. |
| 4,285,964 A | 8/1981 | Niebes et al. |
| 6,491,948 B1 | 12/2002 | Buchholz et al. |
| 8,426,459 B2 | 4/2013 | Stuchlik et al. |
| 2004/0229825 A1* | 11/2004 | Higuchi .................. A61K 45/06 514/27 |
| 2006/0083727 A1* | 4/2006 | Kajander ............. A61K 31/198 424/94.1 |
| 2006/0099239 A1 | 5/2006 | Coleman et al. |
| 2007/0031398 A1* | 2/2007 | Miller .................. A61K 31/733 424/94.63 |
| 2009/0082400 A1 | 3/2009 | Lee et al. |
| 2009/0143317 A1 | 6/2009 | Ono et al. |
| 2009/0149481 A1 | 6/2009 | Azuma |
| 2009/0325906 A1 | 12/2009 | Robbins et al. |
| 2010/0113373 A1 | 6/2010 | Phillips et al. |
| 2010/0204204 A1 | 8/2010 | Zaworotko et al. |
| 2012/0083460 A1 | 4/2012 | Emura et al. |
| 2019/0060272 A1 | 2/2019 | Aleksandrovich et al. |

FOREIGN PATENT DOCUMENTS

| | | |
|---|---|---|
| CN | 101301477 A | 11/2008 |
| DE | 2020/08006741 U1 | 10/2009 |
| DE | 202008006741 U1 | 10/2009 |
| EP | 0075626 A1 | 4/1983 |
| EP | 1669462 A1 | 6/2006 |
| GB | 2198041 A | 6/1988 |
| JP | S59232054 A | 12/1984 |
| JP | 6176552 A | 4/1986 |
| JP | H0654664 A | 3/1994 |

(Continued)

OTHER PUBLICATIONS

Gee, et al. Intestinal Transport of Quercetin Glycosides in Rats Involves Both Deglycosylation and Interaction with the Hexose Transport Pathway[1]. Nutrient Metabolism. 2000. pp. 2765-2771.

(Continued)

*Primary Examiner* — Dale R Miller
(74) *Attorney, Agent, or Firm* — Cesari & McKenna, LLP

(57) ABSTRACT

A composition containing L-arginine and a glycosyl compound of formula (I):

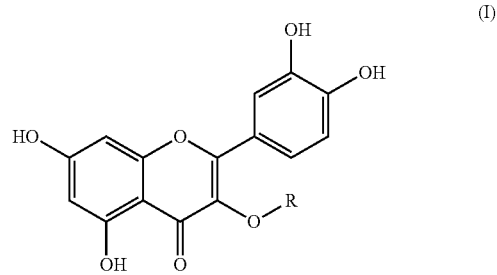

in which R is a moiety formed of a monosaccharide, a disaccharide, or an oligosaccharide including three to five monosaccharides; and the composition contains the glycosyl compound and L-arginine in a molar ratio of 1:1.6 to 1:3.0. Also disclosed is a method for preparing such a composition, as well as a composition prepared by the method.

12 Claims, No Drawings

(56) References Cited

FOREIGN PATENT DOCUMENTS

| | | |
|---|---|---|
| JP | 2003/171274 A | 6/2003 |
| JP | 2005/198642 A | 7/2005 |
| JP | 2007325588 A | 12/2007 |
| JP | 2008092869 A | 4/2008 |
| JP | 2010/126503 A | 6/2010 |
| JP | 2010/248148 A | 11/2010 |
| JP | 2926411-62 | 7/2011 |
| JP | WO2010110328 A1 | 10/2012 |
| JP | 2015/181399 A | 10/2015 |
| JP | 2015208241 A | 11/2015 |
| JP | 2017/131215 A | 8/2017 |
| JP | 2019/024500 A | 2/2019 |
| PT | 1018896 E | 10/2013 |
| RU | 2545905 C1 | 4/2015 |
| RU | 2 545 905 C1 | 10/2015 |
| RU | 2642983 C2 | 1/2018 |
| WO | WO-0012085 A1 | 3/2000 |
| WO | WO-2005030975 A1 | 4/2005 |
| WO | WO-2007114304 A1 | 10/2007 |
| WO | WO-2010/029913 A1 | 3/2010 |
| WO | WO-2010110328 A1 | 9/2010 |
| WO | WO-2011104667 A1 | 9/2011 |
| WO | WO-2019/208574 A1 | 10/2019 |
| WO | WO-2019208574 A1 | 10/2019 |
| WO | WO-2019/230013 A1 | 12/2019 |

OTHER PUBLICATIONS

Acquaviva, et al. Beneficial effects of rutin andL-arginine coadministration in a rat model of liver ischemia-reperfusion injury. Beneficial effects of rutin andL-arginine coadministration in a rat model of liver ischemia-reperfusion injury. Dec. 24, 2008. pp. G664-G670. vol. 296.

Hamad et al "Metabolic Analysis of Various Date Palm Fruit (*Phoenix Dactylifera L.*) Cultivars from Saudi Arabia to Assess Their Nutritional Quality" Molecules vol. 20, pp. 13620-13641, 2015.

Akiyama et al "Constituents of Enzymatically Modified Isoquercitrin and Enzymatically Modified Rutin (Extract)" Journal of the Food Hygienic Society of Japan vol. 41, pp. 54-60, 2000.

Morling et al "Rutosides for Prevention of Post-Thrombotic Sydrome (Review)" Cochrane Database of Systematic Reviews vol. 11, pp. 1-17, 2018.

Morling et al "Rutosides for Treatment of Post-Thrombotic Syndrome (Review)" Cochrane Database of Systematic Reviews vol. 4, pp. 1-26, 2013.

Punithavathi et al "Protective Effects of Rutin on Mitochondrial Damage in Isoproterenol-Induced Cardiotoxic Rats: An *In Vivo* and *In Vitro* Study" Cardiovascular Toxicology vol. 10, pp. 181-189, 2010.

"Preparation of quercetin arginine complex." Weiyu Fu, et al. Chinese Traditional and Herbal Drags. vol. 33, Sec. 8. 2002. pp. 695-697.

Hollman "Determinants of the Absorption of the Dietary Flavonoid Quercetin in Man" State Institute for Quality Control of Agricultural Products, 1997.

Vrijsen et al "Antiviral Activity of Flavones and Potentiation by Ascorbate" Journal of General Virology vol. 69, pp. 1749-1751, 1988.

Yamasaki et al "Flavonoid-Peroxidase Reaction as a Detoxification Mechanism of Plant Cells Against $H_2O_2$" Plant Physiology vol. 115, pp. 1405-1412, 1997.

Abdelkader et al "Investigation into the Emerging Role of the Basic Amino Acid L-Lysine in Enhancing Solubility and Permeability of BCS Class II and BCS Class IV Drugs" Pharm Res vol. 35, pp. 1-18, 2018.

Acquaviva et al. "Beneficial effects of rutin and L-arginine coadministration in a rat model of liver ischemia-reperfusion injury" Am J Physiol Gastrointest Liver Physiol 296 G664-70, 2009.

Çelik et al. "Antioxidant capacity of quercetin and its glycosides in the presence of β-cyclodextrins: Influence of glycosylation on inclusion complexation" J Incl Phenom Macrocycl Chem, 2015, 83:309-319.

Sidra Meer, et al. Efficacy of *Phoenix dactylifera L.* (Date Palm) Creams on Healthy Skin. Cosmetics. May 8, 2017. pp. 1-8.

\* cited by examiner

COMPOSITIONS OF O-GLYCOSYL FLAVONOIDS

CROSS REFERENCE TO RELATED APPLICATIONS

This application is the National Stage of International Application No. PCT/JP2019/017262, filed on Apr. 23, 2019, which claims priority to U.S. Provisional Application Nos. 62/661,255 and 62/720,651, filed on Apr. 23, 2018 and Aug. 21, 2018, respectively. The contents of each application are hereby incorporated by reference in their entirety.

TECHNICAL FIELD

The present invention relates to a compositions of o-glycosyl flavonoids.

BACKGROUND

Flavonoids, abundant in nature, are a class of plant secondary metabolites having variable phenolic structures. Because of their anti-oxidative, anti-inflammatory, and anti-carcinogenic properties, natural flavonoids have attracted much attention across a variety of areas including the pharmaceutical, medical, cosmetic, and nutraceutical industries.

Certain O-glycosyl flavonoids, e.g., isoquercitrin and rutin, exhibit substantial antioxidant effects, thereby making them important additives for food and healthcare products. However, these glycosyl flavonoids have a significant problem, i.e., low water solubility, which greatly restricts their use. For example, when used in the pharmaceutical industry, flavonoids with low water solubility typically exhibit poor pharmacokinetic and therapeutic effects.

To date, two traditional approaches, i.e., invasive and non-invasive, have been used in attempts to improve the water solubility of glycosyl flavonoids. Invasive approaches include chemical or enzymatic modification of the structures of glycosyl flavonoids. See, e.g., Emura et al., US Patent Application 2012/0083460; Hijiya et al., Japanese Patent Application 2926411; and Chabrier et al., U.S. Pat. No. 2,646,428. Non-invasive approaches include salt or co-crystal polymorph formation and an inclusion method. See, e.g., Plungian et al., U.S. Pat. No. 2,451,772; Zaworotko et al., US Patent Application 2010/0204204; and Emura et al., International Application 2010/110328. The invasive approaches generate undesirable analogs of the glycosyl flavonoids that are not in their natural forms. On the other hand, the non-invasive approaches provide modified forms of the glycosyl flavonoids that are typically unstable.

There is a need to develop a new method for producing compositions of glycosyl flavonoids with improved water solubility without the above-described drawbacks.

SUMMARY

An aspect of the present invention is a method of preparing a composition containing L-arginine and a glycosyl compound of formula (I):

Chemical Formula 1

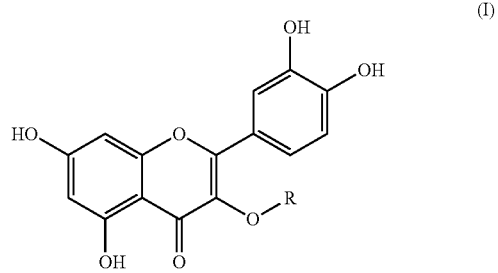

wherein R is a moiety formed of a monosaccharide, a disaccharide, or an oligosaccharide including three to five monosaccharides.

The method includes the following steps: mixing the glycosyl compound with an aqueous solution of L-arginine to form a mixture, in which the glycosyl compound and L-arginine are present in a molar ratio of 1:1.6 to 1:3.0; and agitating the mixture at a temperature of 90° C. or lower.

Typically, the glycosyl compound is isoquercitrin or rutin. The composition preferably contains the glycosyl compound and L-arginine in a molar ratio of 1:1.8 to 1:3.0 (e.g., 1:1.8 to 1:2.8).

It is also preferable that the mixture contains the glycosyl compound and L-arginine at a total concentration of 5 w/v % or higher (e.g., 10 w/v % or higher, 20 w/v % or higher, and 50 w/v % or higher). The aqueous solution of L-arginine generally contains L-arginine at a concentration of 2-10 w/v % (e.g., 2-4 w/v %, 4-6 w/v %, and 6-10 w/v %).

Note that the mixing step can be performed by adding the aqueous solution of L-arginine into a solution of the glycosyl compound in an organic solvent, e.g., ethanol. The agitating step can be performed at 60-90° C. (e.g., 60-80° C. and 70-90° C.).

Another aspect of this invention is a composition containing L-arginine and a glycosyl compound of formula (I) above, in which the the composition is prepared by the steps including: adding the glycosyl compound into an aqueous solution of L-arginine to form a mixture, in which the glycosyl compound and L-arginine are present in a molar ratio of 1:1.6 to 1:3.0; and agitating the mixture at a temperature of 90° C. or lower.

Still within the scope of this invention is a composition containing L-arginine and a glycosyl compound of formula (I):

Chemical Formula 2

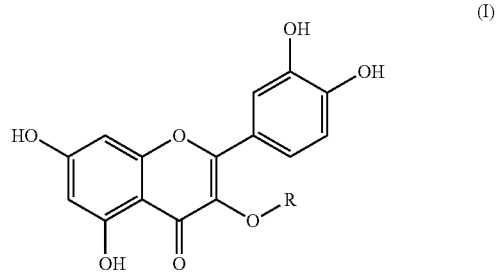

In this formula, R is a moiety formed of a monosaccharide, a disaccharide, or an oligosaccharide including three to five monosaccharides.

The composition of this invention contains the glycosyl compound and L-arginine in a molar ratio of 1:1.6 to 1:3.0.

Notably, the composition described above can further contain a water-soluble antioxidant, a water-soluble vitamin, or a combination thereof. Examples of a water-soluble antioxidant include, but are not limited to, ascorbic acid. Vitamin $B_1$, vitamin $B_3$, and vitamin $B_9$ are among exemplary water-soluble vitamins.

The details of the invention are set forth in the description below. Other features, objects, and advantages of the invention will be apparent from the detailed description of several embodiments, and also from the appending claims.

DETAILED DESCRIPTION

Disclosed first in detail herein is a composition that contains L-arginine and a glycosyl compound of formula (I) depicted in the SUMMARY section above.

To reiterate, in formula (I), R is a moiety formed of a monosaccharide, a disaccharide, or an oligosaccharide including three to five monosaccharides. Examples of a monosaccharide include, but are not limited to, glucose, fructose, and galactose. Examples of a disaccharide include, but are not limited to, rutinose, sucrose, lactose, and maltose.

In one embodiment, the composition contains a glycosyl compound having the R moiety formed of a monosaccharide (e.g., glucose) or a disaccharide (e.g., rutinose). An exemplary glycosyl compound is isoquercitrin or rutin.

Importantly, the composition contains the glycosyl compound and L-arginine in a molar ratio of 1:1.6 to 1:3.0, preferably 1:1.8 to 1:3.0, and more preferably 1:1.8 to 1:2.8.

In the composition, the glycosyl compound is typically present in a content of 10 wt % or higher (e.g., 20 wt % or higher, 30 wt % or higher, and 50 wt % or higher). The glycosyl compound can be in a hydrate form or an anhydrous form. Similarly, the L-arginine also can be in a hydrate form or an anhydrous form.

The composition, either a solid form or an aqueous form, can be in varied formulations for pharmaceutical, medical, or cosmetic use.

In one embodiment, the composition is in an oral formulation selected from one of a liquid, a capsule, a tablet, a pill, and a gel. An exemplary composition is in a capsule or a tablet, each formed from enteric coating. The composition can further contain a pharmaceutically active agent or a pharmaceutically acceptable excipient, or a combination thereof. This embodiment includes a composition that is a pharmaceutical drug, a dietary supplement, a natural health product, a cosmetic product, a food product, or a beverage.

In another embodiment, the composition is in a topical formulation selected from one of a solution, a liniment, a lotion, a cream, an ointment, a paste, a gel, and an emulgel. The composition can further contain a pharmaceutically active agent or a topically acceptable excipient, or a combination thereof. This embodiment includes a composition that is a cosmetic product, a skin care product, or a pharmaceutical drug.

In either an oral formulation or a topical formulation, the above-described composition can further contain a water-soluble antioxidant, a water-soluble vitamin, or a combination thereof. The water-soluble antioxidant is preferably ascorbic acid (i.e., vitamin C) or a structurally close analog thereof, e.g., dehydroascorbic acid. Turning to the water-soluble vitamin, it is preferably vitamin $B_1$ (i.e., thiamine), vitamin $B_3$ (i.e., nicotinic acid), or vitamin $B_9$ (i.e., folic acid).

Further covered by this invention is a method of preparing a composition containing L-arginine and a glycosyl compound of formula (I):

Chemical Formula 3

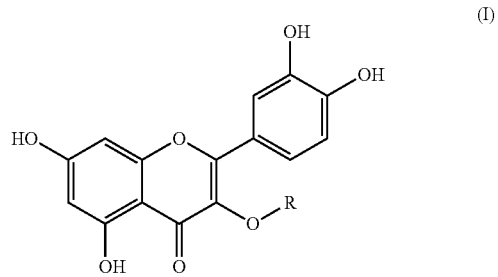

in which R is a moiety formed of a monosaccharide, a disaccharide, or an oligosaccharide including three to five monosaccharides.

Again, the method includes steps (i) mixing the glycosyl compound with an aqueous solution of L-arginine to form a mixture, in which the glycosyl compound and L-arginine are present in a molar ratio of 1:1.6 to 1:3.0; and (ii) agitating the mixture at a temperature of 90 OC or lower.

In this method, the glycosyl compound is preferably either isoquercitrin or rutin. The composition can contain the glycosyl compound and L-arginine in a molar ratio of 1:1.8 to 1:3.0, preferably 1:1.8 to 1:2.8.

It is important that the mixture contains the glycosyl compound and L-arginine at a total concentration of 5 w/v % or higher (e.g., 10 w/v % or higher, 20 w/v % or higher, and 50 w/v % or higher). The term "total concentration" refers to the concentration of the glycosyl compound combined with L-arginine in the mixture thus formed.

The aqueous solution of L-arginine generally contains L-arginine at a concentration of 2-10 w/v % (e.g., 2-4 w/v %, 4-6 w/v %, and 6-10 w/v %).

The materials used in this method, e.g., rutin, isoquercitrin, and L-Arginine, can exist in either an anhydrous form or a hydrate form (e.g., a mono-, di-, or tri-hydrate form). When a material is used in a hydrate form, the water in the hydrate form is included in its molecular weight for calculation.

To form a mixture for preparing the composition of this invention, a glycosyl compound can be added in a solid form into an aqueous solution of L-arginine. Alternatively, the aqueous solution of L-arginine can be added into a solution of the glycosyl compound in a suitable organic solvent. The suitable organic solvent preferably is a water miscible organic solvent, e.g., ethanol.

The mixture thus obtained is agitated at 60-90° C. (e.g., 60-80° C. and 70-90° C.) until the glycosyl compound is fully dissolved to form a homogenous solution. The resulting solution stays at a temperature lower than 60° C. (e.g., room temperature or 25° C.) for a certain period of time, e.g., 12-36 hours.

Unexpectedly, the composition prepared by the method described above exhibits water solubility of a glycosyl compound of formula (I) at least 300 times higher than that of a composition not containing the L-arginine. By contrast, the compositions prepared by conventional methods typically exhibit water solubility of a glycosyl compound 2-40 times higher than that of a composition not containing the L-arginine.

As a result of the significant enhancement of water solubility, compositions of this invention can have superior pharmacokinetic profiles, e.g., oral and dermal absorption, thereby making them suitable for pharmaceutical, medical, or cosmetic use.

Herein, water solubility is determined as the soluble concentration (%) of a glycosyl compound of formula (I), e.g., rutin and isoquercitrin, in an aqueous solution after being left to stand for 24 hours at room temperature. The protocol for determining water solubility is described in EXAMPLE 5 below.

The preparation method demonstrates several advantages, including but not limited to (i) the composition thus obtained can readily release the glycosyl compound in its natural form under an acidic condition, e.g., pH<2.0; (ii) the method can be practically scaled up for large-scale manufacturing; and (iii) it provides an environment-benign process that can be performed in water only.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference in their entirety.

Example 1: Preparation of a Rutin/L-Arginine Composition in Water

A composition containing rutin and L-arginine was prepared in water as follows.

Rutin trihydrate (60 g, 90.4 mmol) was added into a 3 L of aqueous solution containing L-Arginine (45 g, 258.6 mmol) and fully dissolved by agitating at 60° C. Water in the resulting solution was evaporated in vacuo to leave a viscous oil, followed vacuum drying at 60° C. for 8 hours to provide a composition as a yellow orange solid (103.8 g).

Example 2: Preparation of a Isoquercitrin/L-Arginine Composition in Water

A composition containing isoquercitrin and L-arginine was prepared in water as follows.

Isoquercitrin monohydrate (4.73 g, 9.8 mmol) was added into a 50 mL of aqueous solution containing L-Arginine (3.75 g, 21.5 mmol) and fully dissolved by agitating at 80° C. Water in the resulting solution was evaporated in vacuo to leave a viscous oil, followed by vacuum drying at 60° C. for 8 hours to provide a composition as a yellow orange solid (8.38 g).

Example 3: Preparation of a Rutin/L-Arginine Composition in Aqueous Ethanol

A composition containing rutin and L-arginine was prepared in aqueous ethanol as follows.

Rutin trihydrate (2.0 g, 3 mmol) was fully dissolved in ethanol (50 ml) under reflux. An aqueous solution of L-Arginine (1.6 g, 9 mmol) was added into the ethanol solution, followed by agitating at 70° C. for 1 hour. The solvent of the resulting solution was evaporated to leave a solid, which was further dried in vacuo at 60° C. to provide a composition as a deep yellow powder (3.1 g).

Example 4: Preparation of a Isoquercitrin/L-Arginine Composition in Aqueous Ethanol A composition containing isoquercitrin and L-arginine was prepared in aqueous ethanol as follows.

A solution of isoquercitrin monohydrate (1.2 g, 2.5 mmol) in 20 mL ethanol was mixed with an aqueous solution (30 mL) of L-Arginine (1.3 g, 7.5 mmol). The resulting solution was agitated at 70° C. for 1 hour, followed by evaporation of the solvents to leave a solid, which was further dried in vacuo at 60° C. to provide a composition as a yellow orange powder (2.2 g).

Example 5: Water Solubility of Rutin

A study was performed as follows to evaluate the water solubility of rutin from compositions containing rutin and L-arginine in various molar rations.

Rutin trihydrate was added to aqueous solutions of L-arginine at three different concentrations (2.5, 5.0, and 7.1 w/v %). Mixtures of rutin and L-arginine in various molar rations were prepared for an aqueous solution of L-arginine at each of the three concentrations. Each mixture was heated at 80-90° C. for 2 hours. The resulting solution was subsequently left to stand for 24 hours at room temperature. Aliquots of each aqueous solution were centrifuged at 10000 rpm and a HPLC analysis was conducted on each supernatant to measure the rutin concentration. Results are summarized in Tables 1-3 below.

TABLE 1

| | Solubility of rutin with 2.5 w/v % L-arginine in various molar ratios | | | | |
|---|---|---|---|---|---|
| Entry | Molar Ratio rutin/L-arginine | pH | Rutin initial concentration (t = 0) | Rutin concentration (t = 24 h) | Solubility lowering rate (%) |
| 1 | 1:0 No arginine | n$^a$ | — | 0.024% | — |
| 2 | 1:0 No arginine | 7.4$^b$ | — | 0.050% | — |
| 3 | 1:1.6 | 8.8 | 5.7% | 4.2% | 26% |
| 4 | 1:1.8 | 8.7 | 5.0% | 4.8% | 4.0% |
| 5 | 1:2.0 | 8.7 | 4.6% | 4.4% | 4.0% |
| 6 | 1:2.2 | 8.9 | 4.1% | 4.1% | 0% |
| 7 | 1:2.4 | 8.9 | 3.8% | 3.7% | 2.7% |
| 8 | 1:2.6 | 9.0 | 3.6% | 3.5% | 2.8% |
| 9 | 1:2.8 | 9.0 | 3.3% | 3.2% | 3.0% |

$^a$Distilled water was used (n representing a pH value of distilled water).
$^b$Phosphate-buffered saline was used.

TABLE 2

Solubility of rutin with 5.0 w/v % L-arginine in various molar ratios

| Entry | Molar Ratio rutin/L-arginine | pH | Rutin initial concentration (t = 0) | Rutin concentration (t = 24 h) | Solubility lowering rate (%) |
|---|---|---|---|---|---|
| 1 | 1:0 No arginine | n[a] | — | 0.024% | — |
| 2 | 1:0 No arginine | 7.4[b] | — | 0.050% | — |
| 3 | 1:1.6 | 8.9 | 11% | 7.4% | 33% |
| 4 | 1:1.8 | 8.9 | 9.6% | 8.2% | 15% |
| 5 | 1:2.0 | 8.8 | 8.7% | 8.5% | 2% |
| 6 | 1:2.2 | 8.9 | 8.0% | 7.9% | 1% |
| 7 | 1:2.4 | 9.0 | 7.3% | 7.2% | 1% |
| 8 | 1:2.6 | 9.0 | 6.9% | 6.8% | 1% |
| 9 | 1:2.8 | 9.1 | 6.4% | 6.1% | 5% |

[a]Distilled water was used (n representing a pH value of distilled water).
[b]Phosphate-buffered saline was used.

TABLE 3

Solubility of rutin with 7.1 w/v % L-arginine in various molar ratios

| Entry | Molar Ratio rutin/L-arginine | pH | Rutin initial concentration (t = 0) | Rutin concentration (t = 24 h) | Solubility lowering rate (%) |
|---|---|---|---|---|---|
| 1 | 1:0 No arginine | n[a] | — | 0.024% | — |
| 2 | 1:0 No arginine | 7.4[b] | — | 0.050% | — |
| 3 | 1:1.6 | 9.0 | 15% | 11% | 27% |
| 4 | 1:1.8 | 9.0 | 14% | 11% | 21% |
| 5 | 1:2.0 | 8.9 | 13% | 12% | 8% |
| 6 | 1:2.2 | 9.0 | 12% | 12% | 0% |
| 7 | 1:2.4 | 9.0 | 11% | 11% | 0% |
| 8 | 1:2.6 | 9.1 | 9.9% | 10% | 0% |
| 9 | 1:2.8 | 9.2 | 9.3% | 9.6% | 0% |

[a]Distilled water was used (n representing a pH value of distilled water).
[b]Phosphate-buffered Saline was used.

The results shown in Tables 1-3 indicate that, when using aqueous solutions of L-arginine at concentrations of 2.5, 5.0, and 7.1 w/v %, water solubility of rutin was greatly improved for compositions containing rutin and L-arginine in a molar ration of 1:1.8 to 1:2.8.

Example 6: Water Solubility of Isoquercitrin

A study was performed as follows to evaluate the water solubility of isoquercitrin (IQC) from compositions containing isoquercitrin and L-arginine in various molar rations.

Isoquercitrin monohydrate was added to aqueous solutions of L-arginine at three different concentrations (2.5, 5.0, and 7.1 w/v %). Mixtures of isoquercitrin and L-arginine in various molar rations were prepared for an aqueous solution of L-arginine at each of the three concentrations. Each mixture was heated at 80-90° C. for 2 hours. The resulting solution was subsequently left to stand for 24 hours at room temperature. Aliquots of each aqueous solution were centrifuged at 10000 rpm and a HPLC analysis was conducted on each supernatant to measure the isoquercitrin concentration. Results are summarized in Tables 4-6 below.

TABLE 4

Solubility of isoquereitrin with 2.5 w/v % L-arginine in various molar ratios

| Entry | Molar Ratio IQC/L-arginine | pH | IQC initial concentration (t = 0) | IQC concentration (t = 24 h) | Solubility lowering rate (%) |
|---|---|---|---|---|---|
| 1 | 1:0 No arginine | n[a] | — | 0.010% | — |
| 2 | 1:0 No arginine | 7.4[b] | — | 0.028% | — |
| 3 | 1:1.0 | 9.0 | 6.3% | 3.4% | 46% |
| 4 | 1:1.2 | 9.0 | 5.3% | 3.4% | 36% |
| 5 | 1:1.4 | 8.9 | 4.5% | 3.7% | 18% |
| 6 | 1:1.6 | 8.9 | 4.0% | 3.5% | 12% |
| 7 | 1:1.8 | 8.9 | 3.6% | 3.8% | 0% |
| 8 | 1:2.0 | 9.0 | 3.2% | 3.5% | 0% |
| 9 | 1:2.2 | 9.0 | 2.9% | 3.1% | 0% |
| 10 | 1:2.4 | 9.0 | 2.7% | 2.8% | 0% |

[a]Distilled water was used (n representing a pH value of distilled water).
[b]Phosphate-buffered saline was used

TABLE 5

Solubility of isoquereitrin with 5.0 w/v % L-arginine in various molar ratios

| Entry | Molar Ratio IQC/L-arginine | pH | IQC initial concentration (t = 0) | IQC concentration (t = 24 h) | Solubility lowering rate (%) |
|---|---|---|---|---|---|
| 1 | 1:0 No arginine | n$^a$ | — | 0.010% | — |
| 2 | 1:0 No arginine | 7.4$^b$ | — | 0.028% | — |
| 3 | 1:1.0 | 9.2 | 12% | 6.4% | 47% |
| 4 | 1:1.2 | 9.1 | 10% | 6.7% | 33% |
| 5 | 1:1.4 | 9.1 | 8.7% | 6.9% | 4.4% |
| 6 | 1:1.6 | 9.1 | 7.7% | 7.1% | 7.8% |
| 7 | 1:1.8 | 9.1 | 6.9% | 7.1% | 0% |
| 8 | 1:2.0 | 9.1 | 6.3% | 6.4% | 0% |
| 9 | 1:2.2 | 9.2 | 5.7% | 5.8% | 0% |
| 10 | 1:2.4 | 9.3 | 5.3% | 5.4% | 0% |

$^a$Distilled water was used (n representing a pH value of distilled water).
$^b$Phosphate-buffered saline was used.

TABLE 6

Solubility of isoquereitrin with 7.1 w/v % L-arginine in various molar ratios

| Entry | Molar Ratio IQC/L-arginine | pH | IQC initial concentration (t = 0) | IQC concentration (t = 24 h) | Solubility lowering rate (%) |
|---|---|---|---|---|---|
| 1 | 1:0 No arginine | n$^a$ | — | 0.010% | — |
| 2 | 1:0 No arginine | 7.4$^b$ | — | 0.028% | — |
| 3 | 1:1.0 | 9.1 | 17% | 9.4% | 45% |
| 4 | 1:1.2 | 9.1 | 14% | 9.7% | 31% |
| 5 | 1:1.4 | 9.1 | 13% | 9.8% | 25% |
| 6 | 1.1.6 | 9.0 | 11% | 10% | 9.0% |
| 7 | 1:1.8 | 9.1 | 10% | 10% | 0% |
| 8 | 1:2.0 | 9.1 | 9.1% | 9.3% | 0% |
| 9 | 1:2.2 | 9.2 | 8.3% | 8.7% | 0% |
| 10 | 1:2.4 | 9.3 | 7.7% | 7.8% | 0% |

$^a$Distilled water was used (n representing a pH value of distilled water).
$^b$Phosphate-buffered saline was used.

The results shown in Tables 4-6 indicate that, when using aqueous solutions of L-arginine at concentrations of 2.5, 5.0, and 7.1 w/v %, the water solubility of isoquercitrin was greatly improved for compositions containing rutin and L-arginine in a molar ration of 1:1.6 to 1:2.4.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A composition comprising L-arginine and a glycosyl compound selected from the group consisting of isoquercitrin and rutin; and the composition contains the glycosyl compound and L-arginine in a molar ratio of 1:1.8 to 1:2.8.
2. The composition of claim 1, wherein the glycosyl compound is present in a content of 10 wt % or higher.
3. The composition of claim 1, wherein the composition is in an oral formulation selected from the group consisting of a liquid, a capsule, a tablet, a pill, and a gel.
4. The composition of claim 3, wherein the composition is a pharmaceutical drug, a dietary supplement, a natural health product, a cosmetic product, a food product, or a beverage.
5. The composition of claim 4, wherein the composition further contains a water-soluble antioxidant, a water-soluble vitamin, or a combination thereof.
6. The composition of claim 5, wherein the water-soluble antioxidant is ascorbic acid or its edible salt and the water-soluble vitamin is vitamin B1, vitamin B3, or folic acid (vitamin B9), or its edible salt.
7. The composition of claim 3, wherein the composition is in a capsule or a tablet, each formed from enteric coating.
8. The composition of claim 1, wherein the composition is in a topical formulation selected from the group consisting of a solution, a liniment, a lotion, a cream, an ointment, a paste, a gel, and an emulgel.
9. The composition of claim 8, wherein the composition is a cosmetic product, a skin care product, or a pharmaceutical drug.
10. A method of preparing a composition containing L-arginine and a glycosyl compound selected from the group consisting of isoquercitrin and rutin, the method comprising: mixing the glycosyl compound with an aqueous solution of L-arginine to form a mixture, in which the glycosyl compound and L-arginine are present in a molar ratio of 1:1.8 to 1:2.8; and agitating the mixture at a temperature of 60° C. to 90° C.

11. The method of claim 10, wherein the mixture contains the glycosyl compound and L-arginine at a total concentration of 5 w/v % or higher.

12. The method of claim 10, wherein the aqueous solution of L-arginine contains L-arginine at a concentration of 2-10 w/v %.

* * * * *